United States Patent [19]

Heinen

[11] Patent Number: 4,951,368

[45] Date of Patent: Aug. 28, 1990

[54] APPARATUS FOR COMPRESSING MATERIAL INTO A TAMPON

[75] Inventor: Jeffrey L. Heinen, Larsen, Wis.

[73] Assignee: Kimberly-Clark Corporation, Neenah, Wis.

[21] Appl. No.: 383,129

[22] Filed: Jul. 20, 1989

[51] Int. Cl.$^5$ .............................................. A61F 13/20
[52] U.S. Cl. ........................................................ 28/118
[58] Field of Search ......................... 28/118, 119, 120; 100/232

[56] References Cited

U.S. PATENT DOCUMENTS

| | | | |
|---|---|---|---|
| 2,076,389 | 4/1937 | Voss | 18/5 |
| 2,152,230 | 3/1939 | Webb | 18/55 |
| 2,263,909 | 11/1941 | Webb | 18/16 |
| 2,798,260 | 7/1957 | Niepmann et al. | 28/119 |
| 3,103,699 | 9/1963 | Gerard et al. | 18/5 |
| 3,271,502 | 9/1966 | Wentorf, Jr. | 264/320 |
| 3,457,593 | 7/1969 | Basset | 18/16 |
| 4,081,884 | 4/1978 | Johst et al. | 28/119 |
| 4,109,354 | 8/1978 | Ronc | 28/119 |
| 4,498,218 | 2/1985 | Friese | 28/119 |
| 4,685,178 | 8/1987 | Nakanishi | 28/118 |

FOREIGN PATENT DOCUMENTS

| | | | |
|---|---|---|---|
| 2446959 | 4/1976 | Fed. Rep. of Germany | 100/232 |
| 3606150 | 8/1987 | Fed. Rep. of Germany | |
| 1082770 | 9/1967 | United Kingdom | 28/118 |

Primary Examiner—Werner H. Schroeder
Assistant Examiner—Bradley Kurtz De Sandro
Attorney, Agent, or Firm—Thomas J. Connelly

[57] ABSTRACT

An apparatus for compressing a material is disclosed which is particularly useful for forming compressed tampons. The apparatus includes a housing having a first member spaced away from the housing and a second member movable on the housing. Both the first and second members contain die surfaces. A moveable finger is associated with the second member. The moveable finger has a first surface which is biased against the first member and a second surface which cooperates with the die surfaces of the first and second members to form a mold cavity therebetween. The second member is movable so as to cause the mold cavity to vary in volume. Material inserted into the mold cavity can be compressed as the first and second members move towards each other. The compressed product can then be released as the first and second members are moved apart.

34 Claims, 7 Drawing Sheets

APPARATUS FOR COMPRESSING MATERIAL INTO A TAMPON

FIELD OF THE INVENTION

This invention relates to an apparatus for compressing a material, and more particularly, to an apparatus for compressing material into a tampon.

BACKGROUND OF THE INVENTION

Tampons are now widely used for absorbent purposes in the field of feminine hygiene. Currently, there are two basic types: digitally insertable tampons which are designed to be inserted directly by the user's own fingers; and applicator style tampons which are inserted with the aid of an applicator. Both types are usually made by folding or rolling a loosely associated rectangular strip of absorbent material into a blank and then compressing the blank into a cylindrical shaped product known as a pledget. The pledget may or may not contain a cover material, depending upon the manufacturer. A withdrawal string is attached to the pledget before the tampon is wrapped and packaged for sale. The applicator style tampons require an assembly step prior to being wrapped and packaged.

In both digital and applicator style tampons, it is desirable for the tampon to maintain its compressed shape up until its time of use. Furthermore, it is beneficial to compress the pledget to a uniform density so that it has a tendency to expand uniformly as it is being used. Any non-uniform expansion of the tampon could cause leakage which is unacceptable to the final user.

Different apparatuses for compressing absorbent material into tampons are known. U. S. Pat. Nos. 4,685,178; 4,498,218; 4,109,354; 3,271,502 and German patent Nos. 3,605,150 and 2,446,959 relate to various apparatuses used to compress the absorbent material into a desired form. In recent years, many manufacturers have employed a two stage compression technique known in the art as a "pointer-shaper' style compressor. This type of compressor incorporates the use of pointers to pretuck the material into a desired form followed by shapers which give the pledget its final form. One disadvantage of the "pointer-shaper' style compressor is that it involves a two stage operation which does not uniformly compress the product to a uniform density. A second disadvantage is that the two stage method requires complicated equipment which is more difficult to make changes to in order to accommodate different size pledgets. A third disadvantage is that the sequential action of the pointers and shapers results in slower cycle times and therefore a more costly product.

Now an apparatus has been developed which can compress material into a pledget using only one compression step and which is capable of forming a product having a uniform density.

SUMMARY OF THE INVENTION

Briefly, the present invention relates to an apparatus for compressing a material, and more particularly, to an apparatus for compressing one or more materials into a tampon. The apparatus includes a stationary housing, a first member spaced away from the housing, and a second member movable on the housing. Both the first and second members contain die surfaces. A movable finger is associated with the second member and has first and second surfaces. The first surface is biased against the first member and the second surface cooperates with the die surfaces of the first and second members to form a mold cavity therebetween. The second member is movable to permit the mold cavity to vary in volume and allow material to be inserted into the mold cavity and be compressed. The compressed product can then be released from the mold cavity as it again expands.

The general object of this invention is to provide an apparatus for compressing a material. A more specific object of this invention is to provide an apparatus for uniformly compressing material into a tampon.

Another object of this invention is to provide an apparatus which incorporates a single stage of compression for compressing absorbent material into a tampon.

Still, another object of this invention is to provide an apparatus capable of compressing material which is simple in construction, easy to maintain and less expensive to manufacture.

Still further, an object of this invention is to provide an apparatus which can obtain higher cycle rates and thereby operate faster and produce less costly products.

Still further, another object of this invention is to provide an apparatus for compressing material which uses a minimum number of moving parts and is designed to permit easy changeover to accommodate different size products.

Still further, another object of this invention is to provide an apparatus for compressing material into a pledget having a uniform density such that it improves the absorbent potential of the product during use.

Still another object of this invention is to provide an apparatus for compressing material wherein each die member is capable of independent movement.

Other objects and advantages of the present invention will become more apparent to those skilled in the art in view of the following description and the accompanying drawings.

DETAILED DESCRIPTION OF THE PREFERRED EMBODIMENTS

Figure 1:
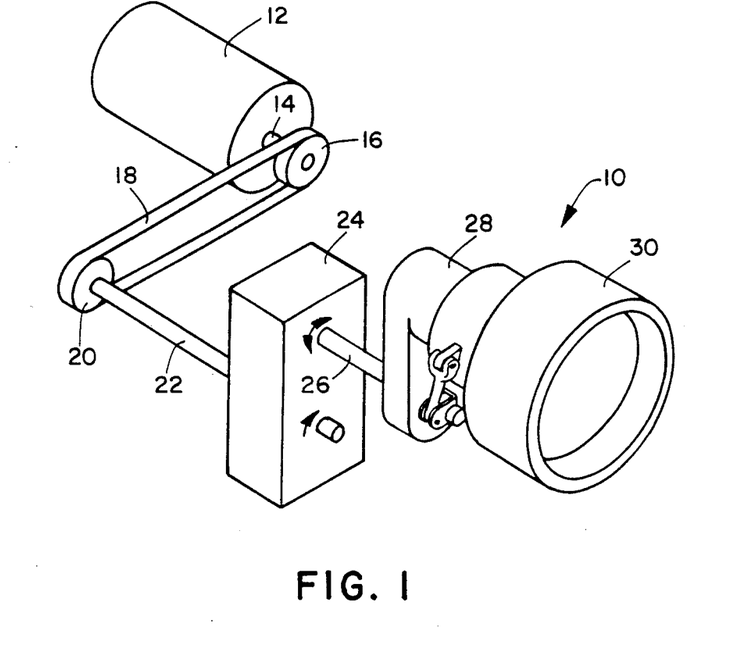
FIG. 1 is an assembly view of an apparatus for compressing material shown connected via an oscillating cam box to an electric motor. The apparatus in FIG. 1 shows the outer ring mounted on a stationary housing without the internal die members.

Referring to FIG. 1, an apparatus 10 for compressing one or more kinds of material into a compressed product is shown. Such an apparatus is especially useful for compressing one or more absorbent materials into a finished tampon pledget. The apparatus 10 can be driven by a mechanical, electrical, electromechanical, pneumatic, or hydraulic mechanism. Likewise, it can be manually operated if desired.

As shown in FIG. 1, a motor 12 having an output shaft 14 supports a pulley 16. The pulley 16 is attached by a belt 18 to a second pulley 20 which in turn is attached to a second shaft 22. The second shaft 22 is connected to an oscillating cam box 24 which has an output shaft 26 extending outwardly therefrom. Various types of cam boxes are commercially available today and oscillating cam boxes are well known in the art. One manufacturer of oscillating cam boxes is Commercial Cam, a division of Emerson Electric Company, 1444 S. Wolf Road, Wheeling, Ill. 60090. The cam boxes are sold under the name Camco.

The apparatus 10 includes a stationary housing 28 which has an outer ring 30 mounted thereto. The output shaft 26 from the cam box 24 is physically connected to the outer ring 30 such that it will cause the outer ring 30 to oscillate as the motor 12 is operated. It should be noted that although the outer ring 30 will be described as oscillating back and forth, one skilled in the art can connect the outer ring 30 to a mechanism which will allow it to be rotated only in one direction while accomplishing the same result. The oscillation of the outer ring 30 causes die members attached to the outer ring 30 to converge as the outer ring 30 is rotated in one direction and to move apart as the outer ring 30 is rotated in an opposite direction. This movement of the die members allows the volume of the mold cavity to vary. Should it be desirable to cause the outer ring 30 to rotate in only one direction, it is possible to use a cam and cam follower arrangement such that the die members will open and close over a certain arc of rotation. For example, for 180° the die members may open and for the remaining 180°. the die members will close.

Figure 2:
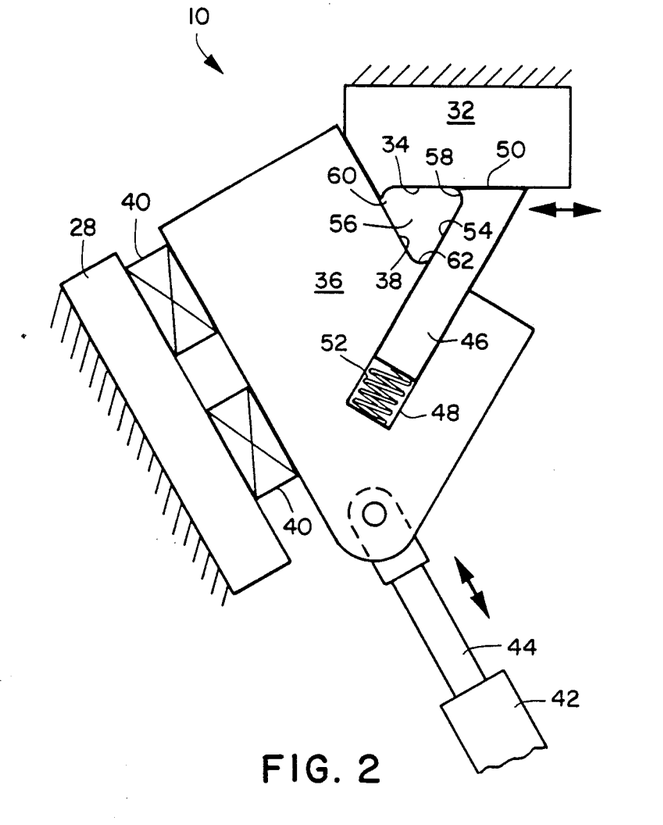
FIG. 2 is an end view of one embodiment of the apparatus for compressing a material showing a stationary die, a movable die, and a movable finger associated with the movable die.

Referring to FIG. 2, an embodiment is shown wherein a first member 32, which preferably is stationary, is spaced away from the housing 28. The first member 32 contains a die surface 34. A second member 36 is movable on the housing 28 and has a die surface 38. The second member 36 can slide relative to the housing 28 on one or more bearings 40. Preferably, the bearings 40 will be linear bearings. The second member 36 can be attached to a drive mechanism 42, such as a motor, via a linkage 44. Preferably, the second member 36 is reciprocated back and forth so that it slides on the bearings 40 relative to the stationary housing 28.

The apparatus 10 further includes a movable finger 46 which is associated with the second member 36. One means of connecting the finger 46 to the second member 36 is to form a cavity or slot 48 in the second member 36 and to insert the finger 46 therein. The finger 46 contains a first surface 50 which is biased against the die surface 34 of the first member 32. The bias means can be a compression spring 52 located at the opposite end of the finger 46. It should be noted that other means for biasing the finger 46 outward away from the second member 36 are known to those skilled in the art. The bias means can include pneumatic and hydraulic devices, as well as electrical type solenoids. The finger 46 further contains a second surface 54 which cooperates with the die surfaces 34 and 38 to form a mold cavity 56 therebetween. The second surface 54 is angularly offset from the first surface 50 by an angle $\theta$ (theta) of between 0° and 180°, preferably, between 0° and 90°, and most preferably, less than 60°. In operation, as the second member 36 slides downward and away from the first member 32, the finger 46 will be forced outward by the compression spring 52 so that the first surface 50 frictionally slides along the die surface 34. This action will cause the volume of the mold cavity 56 to increase such that material can be inserted therein.

In forming a tampon, many types of materials can be utilized which are selected from artificial or natural fibers. These include cotton, polyester, cellulose acetate, nylon, polypropylene and rayon fibers, as well as blends thereof. Other materials can also be utilized. The strips of material which are to be compressed can be radially wound into a cylindrical shape or be made from folding absorbent materials together. It is also possible to stack several sheets of material together before loosely winding them up into a cylindrical shape. One suitable blend includes 5-10% cotton combined with 90-95% rayon fibers. Sometimes, a tampon will consist of the absorbent material covered by a thin outer cover or layer consisting of a blend of polypropylene and rayon fibers. The finished tampon should have a rigid enough consistency so as to be inserted into a woman's vagina without deformation. However, the tampon must also have the ability to swell or enlarge when it comes in contact with body fluid so as to prevent leakage of fluids while in use.

The apparatus shown in FIG. 2 is capable of uniformly compressing absorbent material into a tampon pledget by permitting the second member 36 and the finger 46 to simultaneously move against and adjacent to the first member 32. This movement causes the die surfaces 34, 38 and 54 to converge and decreases the volume of the mold cavity 56. In so doing, the die surface 38 may slidably contact a second surface of the first member 32. However, in order to avoid friction and heat, it is preferred that only slidable contact be made. Preferably, enough clearance should be present between the surfaces to minimize friction, while at the same time preventing material contained in the mold cavity 56 from squeezing between the two surfaces. As the mold cavity 56 is decreased in volume, the absorbent material contained therein will be compressed by the three die surfaces 34, 38 and 54 and a pledget will be formed having a uniform density.

In FIG. 2, the mold cavity 56 is shown with an approximately triangular cross-sectional configuration. It should be noted that the shape of the mold cavity can be selected to suit one's specific needs. If desired, it is possible to form a radius on the second surface 54 of the finger 46 adjacent to the die surface 34. A radius 60 can also be formed on the die surface 34 at a point adjacent to the point of contact with the second member 36. Likewise, a radius 62 can be formed on the second member 36 adjacent to a point of contact with the finger 46. The radiuses 58, 60 and 62 will cooperate with the adjacent die surfaces 34, 38 and 54 to define a mold cavity 56 having a triangular cross-sectional configuration with rounded apexes. A pledget formed in such a mold cavity may be more aesthetically appealing to the end user than a pledget having sharp corners.

Figure 3:
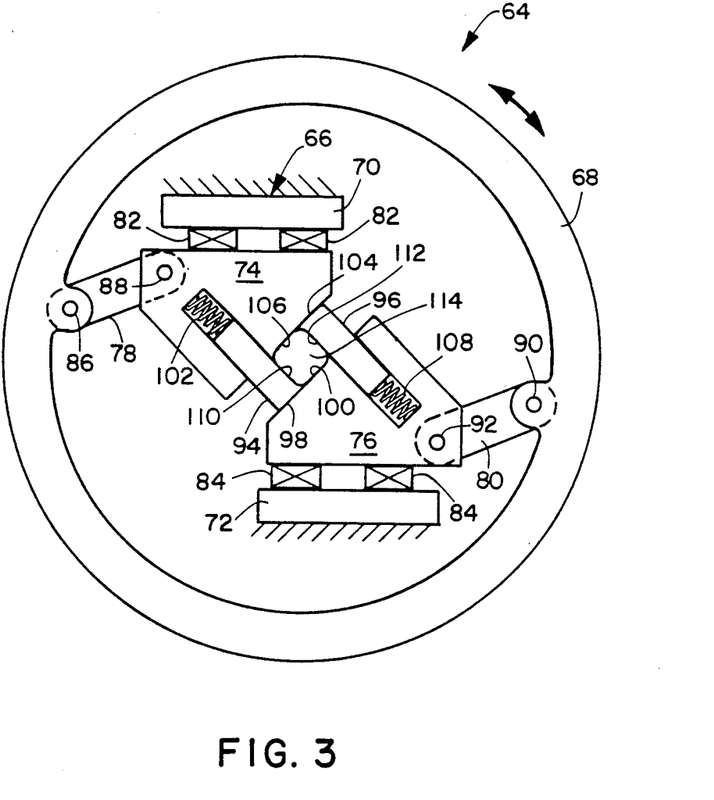
FIG. 3 is a second embodiment of the apparatus showing an end view of the compressor having a pair of movable die members each having a movable finger associated therewith.

Referring to FIG. 3, an alternative embodiment is shown wherein an apparatus 64 is depicted having a housing 66 and a movable outer ring 68 associated therewith. Preferably, the housing 66 is stationary and the outer ring 68 oscillates relative to the housing 66. The housing 66 is shown having two spaced apart arms 70 and 72 which support first and second movable members 74 and 76. The first and second members 74 and 76 are each pivotally connected to the outer ring 68 by toggle linkages 78 and 80, respectively. As depicted, the first and second members 74 and 76 can slide on bearings 82 and 84, respectively, affixed to the stationary arms 70 and 72. The toggle linkages 78 and 80 contain pivot attachments at each end 86 and 88, and 90 and 92, respectively, such that the first and second members 74 and 76 can move toward one another as the compressive forces approach their greatest value. For example, the compressive forces will approach their greatest value when the linkages 78 and 80 are moved into coaxial alignment with one another. This results in a mechanical advantage to the outer ring 68.

A first movable finger 94 is associated with the first member 74 and a second movable finger 96 is associated with the second member 76. The fingers 94 and 96 are configured and function the same way as the finger 46 discussed above. The finger 94 contains a first surface 98 which is slidable with a die surface 100 formed on the second member 76. The first surface 98 is biased into constant contact with the die surface 100 by a compression spring 102. The second finger 96 contains a first surface 104 which is slidable with a die surface 106 formed on the first member 74. The first surface 104 is biased into constant contact with the die surface 106 by a compression spring 108. It should be noted that the springs 102 and 108 will bias the fingers 94 and 96, respectively, outwardly away from the first and second members 74 and 76, respectively. Each of the fingers 94 and 96 also contain a second surface 110 and 112, respectively, which are angularly offset from the first surfaces 98 and 104, respectively. The second surfaces 110 and 112 cooperate with the die surfaces 100 and 106 to form a mold cavity 114 therebetween.

The mold cavity 114, as shown in FIG. 3, has an approximately square cross-sectional configuration. However, the cross-sectional configuration can be altered to a rectangular shape should the first and second members 74 and 76 be spaced farther apart, or if the fingers 94 and 96 are positioned differently. It is also possible to form radiuses on the second surfaces 110 and 112 and on the die surfaces 100 and 106, as explained above, so as to form a compressed pledget having rounded corners.

The apparatus 64 is designed to operate such that as the outer ring 68 is rotated in one direction, the first and second members 74 and 76 will approach one another. This causes the fingers 94 and 96 to compress the springs 102 and 108, respectively, as they slide on the die surfaces 100 and 106, respectively. This action will cause the volume of the mold cavity 114 to decrease and compress any material which is present therein. As the outer ring 68 is oscillated or rotated in a reverse direction, the first and second members 74 and 76 will move away from one another thereby permitting the fingers 94 and 96 to move outward via the force of the springs 102 and 108, respectively. As this occurs, the volume of the mold cavity 114 will increase thereby permitting the compressed product to be removed from the mold cavity 114. Likewise, new material can be inserted into the enlarged mold cavity 114 so that it can be compressed on the next compression stroke.

As stated above, the apparatus 64 has the ability to compress material uniformly. The amount of compression and the specific density to which the material is compressed can be adjusted depending upon the type of pledget one desires. Laboratory tests have proven that a pledget having a uniform density has a better gram/gram absorbency rate and is capable of exhibiting a consistent volumetric expansion while in use.

Figure 4:
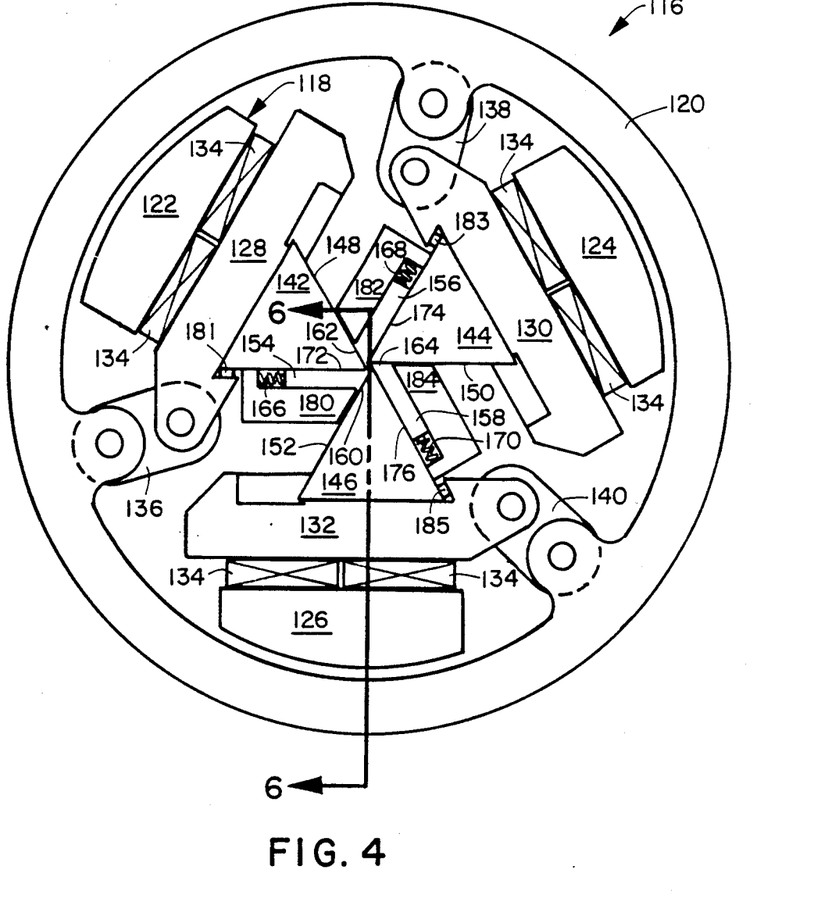
FIG. 4 is a third embodiment of the apparatus showing an end view wherein three movable dies cooperate to form a mold cavity. The die members are shown in their closed position.
Figure 5:
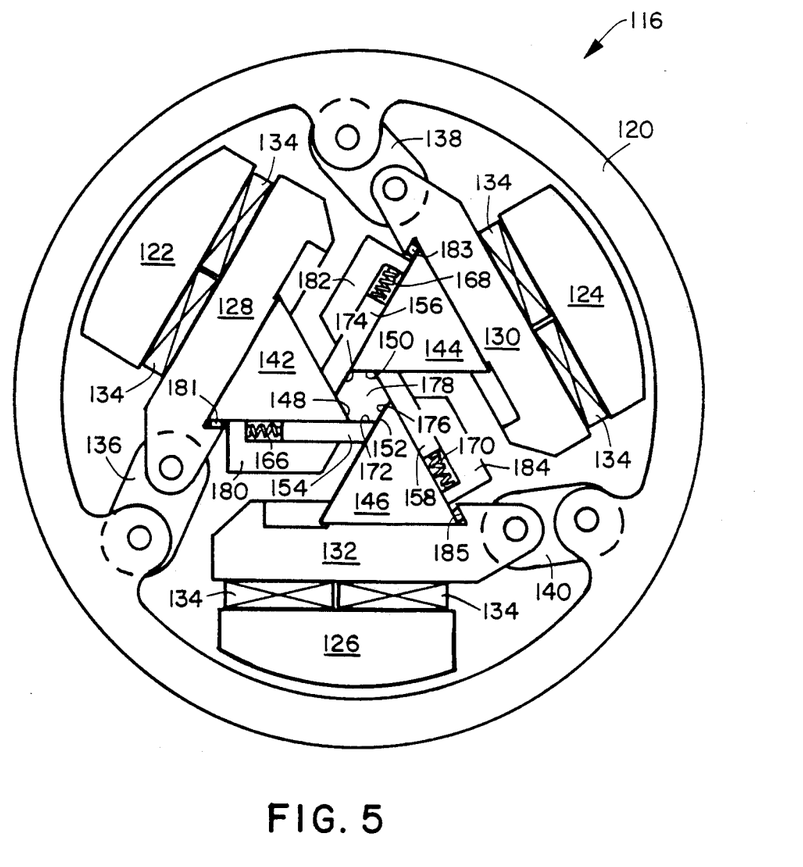
FIG. 5 is an end view of the apparatus shown in FIG. 4 except that the die members are shown in their open position.

Referring to FIGS. 4 and 5, another embodiment is shown wherein an apparatus 116 contains a stationary housing 118 and a movable outer ring 120. The housing 118 has three spaced apart arms 122, 124 and 126. The arms 122, 124 and 126 are located approximately 120 degrees apart. Carriages 128, 130, and 132 are slidably mounted onto the arms 122, 124 and 126, respectively, by bearings 134. Each carriage 128, 130 and 132 is also pivotally connected to the outer ring 120 by toggle linkages 136, 138 and 140, respectively. Preferably, each linkage 136, 138 and 140 is pivotally attached at one end to the outer ring 120 and at an opposite end to one of the carriages 128, 130 and 132. Each carriage 128, 130 and 132 has a die 142, 144 and 146, respectively, secured thereto and each die 142, 144 and 146 has a die surface 148, 150 and 152, respectively. The carriages 128, 130 and 132 and the attached dies 142, 144 and 146 are arranged in a circular array around a central axis passing through the outer ring 120.

As the outer ring 120 is oscillated or rotated in opposite directions, the dies 142, 144, and 146 will move towards and away from one another. Each die 142, 144 and 146 has a movable finger 154, 156 and 158, respectively, associated therewith. Each of the movable fingers 154, 156 and 158 has a first surface 160, 162 and 164, respectively, which is biased outwardly, for example, by a compression spring 166, 168 and 170, respectively. Each finger 154, 156 and 158 also contains a second surface designated 172, 174 and 176, respectively, which is angularly offset by an angle from the first surface 160, 162 and 164 and cooperates with the die surfaces 148, 150 and 152 to form a mold cavity 178 therebetween.

The mold cavity 178, best shown in FIG. 5, shows the dies 142, 144 and 146 in the open position. The mold cavity 178 is in the form of a hexagon having six flat sides. However, it should be noted that the die surfaces and the second surfaces of the fingers 154, 156 and 158 can be concave, convex or contoured so as to form a circular mold cavity having a polygon shape. It should also be pointed out that in FIGS. 4 and 5, the fingers 154, 156 and 158 are not formed in the dies 142, 144 and 146 respectively, but instead are attached to the dies 142, 144 and 146 via retainers 180, 182 and 184, respectively. Shims 181, 183 and 185 can be positioned between the carriages 128, 130 and 132 and the dies 142, 144 and 146, respectively. The shims 181, 183 and 185 present an easy way to vary the size of the mold cavity 178 so as to accommodate more or less material to form different size pledgets. The shims 181, 183 and 185 represent one simplistic way of varying the size of the mold cavity 178 without incorporating additional moving parts or requiring extensive readjustment of existing components.

The apparatus 116 also contains means for oscillating the outer ring 120 to cause the mold cavity 178 to vary in volume. As the outer ring 120 is rotated in one direction, the mold cavity 178 is enlarged to an open position and material can be inserted into it. The outer ring 120 is then rotated in an opposite direction and the mold cavity 178 closes so as to compress the material which has been inserted into it. The mold cavity 178 is again reopened by again rotating the outer ring 120 in the first direction and this permits the compressed material to be released. The apparatus 116 has the unique distinction of being able to uniformly compress material inserted into the mold cavity 178 to a uniform density in a single operation.

Figure 6:
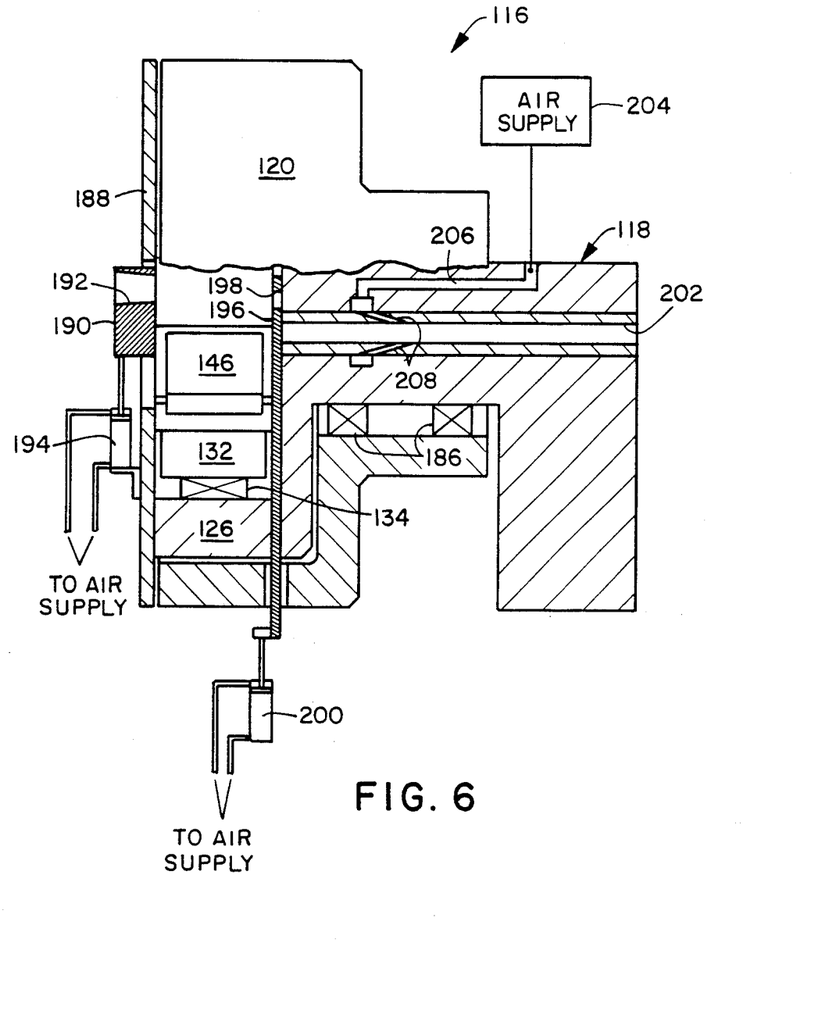
FIG. 6 is a partial cross-sectional view of the apparatus shown in FIG. 4, taken along line 6—6, and reveals the internal mechanism for routing a tampon blank into and out of the compression chamber.

Referring to FIG. 6, a side view of the apparatus 116 is shown wherein the outer ring 120 is movably mounted on the stationary housing 118 by bearings 186. Within the outer ring 120 is shown one of the arms 126 having a carriage 132 which is slidable on the bearing 134. The die 146 is secured to the carriage 132. Although only die 146 is shown, the other two dies 142 and 144 cooperate with the die which is shown to form a mold cavity along the horizontal central axis of the drawing. The mold cavity is closed at one end by a front plate 188 which has a gate 190 associated therewith. The gate 190 contains an input port 192 and is movable in an arcuate fashion by an air cylinder 194. In one position, the input port 192 will line up with the horizontal central axis and permit material to be inserted into the mold cavity. After the material is inserted into the mold cavity, the gate 190 is rotated along its arcuate path by the air cylinder 194 such that the input port 192 is rotated out of position with the horizontal central axis thereby closing off one end of the mold cavity. The opposite end of the mold cavity has a backgate 196 positioned adjacent to it. The backgate 196 contains an output port 198 and is designed to be reciprocated up and down by an air cylinder 200. When the backgate 196 is in its up position, the mold cavity is blocked and when the backgate 196 is lowered to its down position, the output port 198 is in axial alignment with the horizontal central axis of the housing 118. The housing 118 also contains a passageway 202 which is axially aligned with the horizontal axis of the mold cavity. An air supply device 204 is connected to the passageway 202 via conduits 206 and a plurality of interconnected air ports 208, only two of which are shown. The air ports 208 are angled away from the mold cavity.

In operation, absorbent material is inserted through the input port 192 and into the mold cavity while the backgate 196 blocks the passageway 202. The front gate 190 is then moved to a closed position, closing off the entire mold cavity. The outer ring 120 is rotated in one direction causing the die members 142, 144 and 146 to converge and compress the material to form a compressed pledget. The outer ring 120 is then rotated in an opposite direction causing the dies 142, 144 and 146 to move away from one another. It is envisioned that the time required to compress the material may be very short, for example in milliseconds, and that the apparatus 116 can operate at various speeds. The compression will take place at room temperature and the material can be compressed at a force of from between 1 to several hundred pounds per square inch (psi). The mold cavity can vary in diameter to suit the product being compressed. For tampons, the distance can be between 0.25 and 2 inches. The torque required on the outer ring 120 for compressing the material can also vary. For tampons, the range can be from 1 to 10,000 inch pounds, preferably, between 3 and 5,000 inch pounds.

The dies 142, 144 and 146 are assembled such that they can move simultaneously, although each can move independent of one another. The independent movement prevents breakage of the parts. For example, should one of the carriages 128, 130 and 132 bind up on the bearings 134, its respective die 142, 144 and 146 will stop moving while the other two dies can move as designed.

Once the compressed tampon pledget is formed, the backgate 196 is lowered so that the output port 198 is in coaxial alignment with the passageway 202. Pressurized air from the air supply device 204 will then create a vacuum on one end of the pledget and cause it to be transported through the passageway 202 and out of the housing 118. It should be noted that although an air transport system has been shown, other types of devices can be used to insert or remove the pledget. After the pledget is removed from the housing, it is normally directed to a heat set cavity where the temperature is raised. At this higher temperature, the hexagonal shape of the pledget will expand to an approximate circle. The finished tampon will have a generally elongated cylindrical shape and the insertion end can be tapered into the shape of a bullet if desired.

Figure 7:
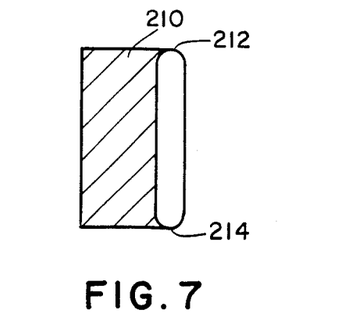
FIGS. 7, 8 and 9 show three various die contours for forming variously configured pledgets.
Figure 8:
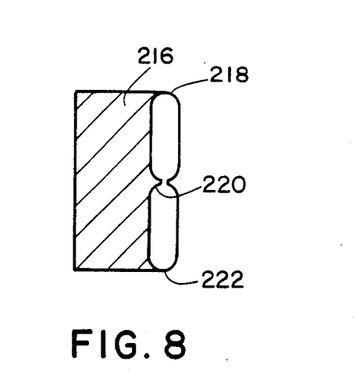
Figure 9:
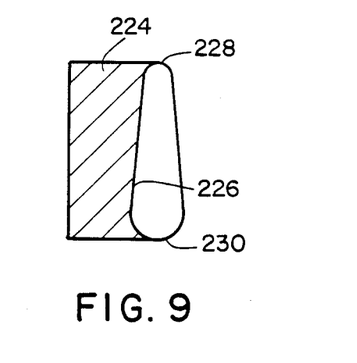

Referring to FIGS. 7, 8 and 9, various examples of die contours are shown. The contour of the die will configure the outer surface of the compressed pledget. In FIG. 7, a die 210 is shown having two spaced apart lips 212 and 214. The lips 212 and 214 form rounded ends on the pledget. In FIG. 8, a die 216 is shown having three spaced apart lips 218, 220 and 222, respectively. These lips form a pledget with rounded ends and a narrow center section. This pledget can be cut in half to form two finished size pledgets. Each of the two pledgets would have rounded ends. It should be noted that it is possible to form the die surface such that three or more tampons can be formed at one time. Lastly, FIG. 9 shows a die 224 having a contoured surface 226 formed between spaced apart lips 228 and 230. The contour surface forms a compressed pledget which is thicker on one end than at the opposite end. Although only three alternative embodiments are shown, it should be noted that other shapes for the die surfaces are possible.

It should be noted that from a cost point of view, it would be advantageous to insert material into the mold cavity which would have a width which would enable the compressed pledget to be later cut into two or more finished tampons. This method would increase cycle time and reduce cost.

While the invention has been described in conjunction with several specific embodiments, it is to be understood that many alternatives, modifications, and variations will be apparent to those skilled in the art in light of the foregoing description. Accordingly, this invention is intended to embrace all such alternatives, modifications and variations which fall within the spirit and scope of the appended claims.

I claim:

1. An apparatus for compressing material to form a compressed product comprising:
   (a) a housing;
   (b) a first member spaced away from said housing having a die surface;
   (c) a second member movable on said housing having a die surface;
   (d) a movable finger associated with said second member having a first surface which is biased against said first member and a second surface which cooperates with said die surfaces of said first and second members to form a mold cavity therebetween; and (e) means for moving said second member causing said mold cavity to vary in volume whereby material inserted in said mold cavity can be compressed into a compressed product and then be released from said mold cavity.

2. The apparatus of claim 1 wherein said first member is stationary.

3. The apparatus of claim 2 wherein said second member is slidable relative to said first member and said finger is in constant contact with said die surface of said first member.

4. The apparatus of claim 1 wherein said first and second members move simultaneously to uniformly compress said material.

5. The apparatus of claim 4 wherein said material is compressed to a uniform density.

6. The apparatus of claim 1 wherein said means for moving said second member is a motor.

7. An apparatus for compressing material to form a compressed product comprising:
   (a) a housing;
   (b) a first member spaced apart from said housing having a die surface;
   (c) a second member slidable on said housing having a die surface;
   (d) a movable finger associated with said second member having a first surface which is biased against said die surface of said first member and a second surface which cooperates with said die surfaces of said first and second members to form a mold cavity therebetween, and
   (e) means for reciprocating said second member causing said mold cavity to vary in volume whereby material inserted in said mold cavity can be compressed into a compressed product and then be released from said mold cavity.

8. The apparatus of claim 7 wherein said mold cavity uniformly compresses said product.

9. The apparatus of claim 7 wherein said mold cavity has an approximately triangular cross-sectional configuration.

10. The apparatus of claim 7 wherein said movable finger is spring biased outward from said second member.

11. The apparatus of claim 10 wherein said first surface of said finger is in constant contact with said first member.

12. The apparatus of claim 10 wherein said first surface of said finger is slidable on said die surface of said first member.

13. The apparatus of claim 7 wherein said die surfaces of said first and second members are angularly offset by at least 60 degrees.

14. The apparatus of claim 7 wherein said second surface of said finger contains a radius adjacent said first surface, said die surface of said first member contains a radius adjacent a point of contact with said second member, and said die surface of said second member contains a radius adjacent a point of contact with said finger, said radiuses cooperating with said adjacent surfaces to define a mold cavity having a triangular cross-sectional configuration with rounded apexes.

15. An apparatus for compressing material to form a tampon comprising:
   (a) a housing having two spaced apart arms;
   (b) a movable ring mounted on said housing;
   (c) first and second members each pivotally connected to said ring and each being movable relative to one of said arms, each member having a die surface;
   (d) a movable finger associated with said first and second members, each of said fingers having a first surface which is
   biased against said die surface of said other member and a second surface which cooperates with said die surfaces of said first and second members to form a mold cavity therebetween; and
   (e) means for oscillating said ring causing said mold cavity to vary in volume whereby material inserted in said mold cavity can be compressed into a tampon and said compressed tampon can be released from said mold cavity 16. The apparatus of claim 15 wherein said mold cavity has an approximately square cross-sectional configuration.

17. The apparatus of claim 15 wherein said die surfaces and said second surfaces of said fingers combine to exert a uniform pressure on said material inserted into said mold cavity to form a uniformly compressed tampon.

18. The apparatus of claim 15 wherein said first surface of each finger is in constant contact with said die surface of said other member.

19. The apparatus of claim 15 wherein said first and second members are pivotally connected to said ring.

20. The apparatus of claim 19 wherein each of said linkages is pivotally connected at one end to said ring and at an opposite end to on of said members.

21. The apparatus of claim 15 wherein said means for oscillating said ring is a motor.

22. The apparatus of claim 21 wherein said motor is connected to said ring by a cam box.

23. The apparatus of claim 15 wherein said first and second members are angularly offset.

24. The apparatus of claim 15 wherein said fingers are spring biased outward from said respective members.

25. The apparatus of claim 24 wherein said fingers cause said springs to be compressed as said members are moved toward one another.

26. An apparatus for compressing material to form a tampon comprising:
   (a) a stationary housing;
   (b) a movable ring;
   (c) a plurality of members arranged in a circular array around a central axis and having a die surface spaced apart from the central axis, said members being pivotally connected to said ring and slidable on said housing, said members capable of moving toward and away from the central axis as said ring is rotated in opposite directions;
   (d) a movable finger associated with each of said members, each of said fingers having a first surface which is biased against said die surface of an adjacent member and a second surface which cooperates with said die surfaces of said members and said second surfaces of said other fingers to form a mold cavity therebetween; and
   (e) means for oscillating said ring causing said mold cavity to vary in volume whereby material inserted in said mold cavity can be compressed into a compressed tampon and then be released from said mold cavity.

27. The apparatus of claim 26 wherein there are at least three members arranged about said central axis.

28. The apparatus of claim 27 wherein said members are angularly offset by approximately 120 degrees.

29. The apparatus of claim 26 wherein said mold cavity compressed said material to a uniform density.

30. An apparatus for compressing material to form a tampon comprising:
 (a) a housing;
 (b) a movable ring mounted on said housing;
 (c) at least three members arranged in a circular array around a central axis, each member being pivotally connected to said ring and slidable on said housing;
 (d) a die secured to each of said members, each die having a die surface spaced apart from the central axis and being capable of moving toward and away from the central axis as said ring is rotated in opposite directions;
 (e) a movable finger associated with each of said dies, each finger having a first surface which is biased against said die surface of an adjacent die and a second surface which cooperates with said die surfaces and said second surfaces of said other fingers to form a mold cavity therebetween; and
 (f) means for oscillating said ring causing said dies to converge and compress material inserted in said mold cavity into a compressed tampon and for moving said dies apart thereby enabling said compressed tampon to be removed from said mold cavity.

31. The apparatus of claim 30 wherein said fingers are spring biased outward from said respected die.

32. The apparatus of claim 31 wherein said fingers cause said springs to be compressed as said dies are moved toward one another.

33. The apparatus of claim 30 wherein said mold cavity has an approximately hexagonal cross sectional configuration.

34. The apparatus of claim 31 wherein said mold cavity compresses said material to a uniform density.

* * * * *